US007226590B2

(12) United States Patent
Chilcott et al.

(10) Patent No.: US 7,226,590 B2
(45) Date of Patent: Jun. 5, 2007

(54) ANTIMICROBIAL COMPOSITION

(75) Inventors: Christopher Norman Chilcott, Dunedin (NZ); John Robert Tagg, Dunedin (NZ)

(73) Assignee: BLIS Technologies Limited, Dunedin (NL)

( * ) Notice: Subject to any disclaimer, the term of this patent is extended or adjusted under 35 U.S.C. 154(b) by 0 days.

(21) Appl. No.: 10/505,001

(22) PCT Filed: Feb. 21, 2003

(86) PCT No.: PCT/NZ03/00031

§ 371 (c)(1),
(2), (4) Date: Aug. 18, 2004

(87) PCT Pub. No.: WO03/070419

PCT Pub. Date: Aug. 28, 2003

(65) Prior Publication Data

US 2005/0079597 A1    Apr. 14, 2005

(30) Foreign Application Priority Data

Feb. 22, 2002  (NZ) ..................................... 517398

(51) Int. Cl.
*A01N 63/00* (2006.01)
*A61K 39/00* (2006.01)
*A61K 39/395* (2006.01)

(52) U.S. Cl. ............... 424/93.44; 424/93.4; 424/165.1; 424/164.1; 424/130.1; 424/184.1

(58) Field of Classification Search ............... 424/93.4, 424/93.44, 165.1, 164.1, 130.1, 184.1
See application file for complete search history.

(56) References Cited

U.S. PATENT DOCUMENTS 3,925,160 A    12/1975  Sanders, Jr. et al.
2004/0232205 A1*  11/2004  Tagg et al. ................. 228/101

FOREIGN PATENT DOCUMENTS

| EP | 0524732 A2 | 6/1992 |
| WO | WO 00/05972 | 2/2000 |
| WO | WO 01/27143 | 4/2001 |

OTHER PUBLICATIONS

James et al (The prevention of dental caries by BLIS-mediated inhibition of mutans Streptococci, New Zealand Dental Journal, 1991; 87: 80-83).*
Soderling et al (Influence of maternal xylitol consumption on mother-child transmission of mutans streptococci: 6-year follow-up, 2001;35: 173-77).*
Balakrishnan et al (Diverse activity spectra of bacteriocin like inhibitory substances having activity against mutans streptococci, Caries Research, 2001;35: 75-80).*
Ross, et al (Isolation and characterization of the lantibiotic salivaricin A and its structural gene salA from *Streptococcus salivarius* 20P3, Applied and Environmental Microbiology, 1993;59(7): 2014-21).*
Tanzer et al., "Competitive Displacement of Mutans Streptococci and Inhibition of Tooth Decay by *Streptococcus salivarius* TOVE-R," *Infection and Immunity*, Apr. 1985, vol. 48, No. 1.
Tanzer et al., "Inhibition of Ecological Emergence of Mutans Streptococci Naturally Transmitted Between Rats and Consequent Caries Inhibition By *Streptococcus salivarius* TOVE-R Infection," Infection and Immunity, vol. 49, No. 1, pp. 76-83, 1985.
Dempster et al., "The Production of Bacteriocin-like Substances by the Oral Bacterium *Stretococcus salivarius*," *Archives or Oral Biology*, vol. 27, pp. 151 to 157, 1982.
Balakrishnan, et al., "Diverse Activity Spectra of Bacteriocin-like Inhibitory Substances Having Activity Against Mutans Streptococci," *Caries Research*, 35: pp. 75-80, 2001.
Hillman, et al., "Colonization of the Human Oral Cavity," *Journal of Dental Research*, vol. 66(6), pp. 1092-1094, Jun. 1987.
James, et al., "The Prevention of Dental Caries by BLIS-mediated Inhibition of Mutans Streptococci," *New Zealand Dental Journal*, vol. 87, pp. 80-83, 1991.
Nagawa, et al., "Preparation of the Bifidus Milk Powder," *Journal of Dairy Science*, vol. 71, pp. 1777-1782, 1988.
Thompkins, "Antagonistic Interactions among Numerically Prominent Members of the Human Oral Microbiota," *A thesis submitted for the degree of Doctor of Philosophy at the University of Otago, Dunedin, New Zealand*, 1986.
Thompkins, et al., "Bacteriocin-like Inhibitory Activity Associates with Beta-hemolytic Strains of *Streptococcus salivarius*," *Journal of Dental Research*, vol. 66, No. 8, pp. 1321-1325, 1987.
Thompkins, et al., "The Ecology of Bacteriocin-producing Strains of *Streptococcus salivarius*," *Microbial Ecology in Health and Disease*, vol. 2, pp. 19-28, 1989.
Kurasz A. B. et al., "In vitro studies of growth and competition between *S. salivarius* TOVE-R and *mutans streptococci*;" Journal of Dental Research, Sep. 1996, vol. 65, No. 9, pp. 1149-1153.

* cited by examiner

*Primary Examiner*—Robert A. Zeman
*Assistant Examiner*—Lakia J. Tongue
(74) *Attorney, Agent, or Firm*—Frommer Lawrence & Haug LLP

(57) ABSTRACT

This invention provides novel *Streptococcus salivarius*, compositions containing same, and use of *S. salivarius* strains as antimicrobial agents. The strains are bacterial inhibitors with respect to at least *S. mutans* and/or MS and therefore have a number of therapeutic applications. The applications include but are not limited to forming part of therapeutic formulations for use in controlling, treating, or preventing dental caries.

25 Claims, No Drawings

ANTIMICROBIAL COMPOSITION

FIELD OF THE INVENTION

This invention relates to novel *Streptococcus salivarius*, compositions containing same, and use of *Streptococcus salivarius* strains as antimicrobial agents, particularly in the prevention or treatment of dental caries.

BACKGROUND

Dental caries is a disease characterised by dissolution of the mineral portion of the tooth. As caries progresses, destruction of tooth enamel and dentine occurs followed by inflammation of pulp and periapical tissues.

The mutans streptococci (MS) are a cluster of acidogenic, dental plaque-inhabiting streptococcal species that are considered the principal causative agents of caries. Presently, seven different MS species (known as *S. mutans*, *S. rattus*, *S. cricetus*, *S. sobrinus*, *S. ferns*, *S. macacae*, and *S. downei*) are recognised. Of these seven species it is mainly *S. mutans* and *S. sobrinus* that are of significance in terms of human caries.

Over the years various methods have been developed and tried with varying results, to prevent or at least alleviate the problem of dental caries. Treatments with antibiotics such as penicillin have been suggested and are effective but indiscriminately destroy both useful and harmful bacteria in the mouth leading to microbial imbalances.

In order to minimise disruption to the mouth microflora, antibiotic producing organisms have been investigated for their ability to inhibit caries. A group of organisms identified as having potential in this regard are microorganisms producing bacteriocin-like inhibitory substances (BLIS). BLIS producers of the genera *Streptococcus, Staphylococcus* and *Enterococcus* have been screened for potential application to prevention of dental caries (Balakrishnan, M. et al., Caries Res. 2001; 35:75–80).

What is sought is a non-virulent analog of the disease-causing *S. mutans*, or a so called effector strain. To serve as an effector strain in replacement therapy in bacterial infection, the microorganism must be non-virulent itself and able to compete successfully with the pathogenic microorganism either via competitive action and/or antibiotic action. *S. mutans* effector strains have been identified (Hillman et al, J Dent Res. 1987; 66:109–24; James and Tagg, N Z Dent J. 1991; 87:80–3) and show strong anti-*S. mutans* activity. A disadvantage with the use of *S. mutans* effector strains is the cariogenic potential of these strains.

*S. salivarius* is an alternative *streptococcus* species which avoids this disadvantage. In WO 01/27143 *S. salivarius* strains are identified which have utility in the treatment of dental caries caused at least in part by *S. sobrinus*. No activity was recorded against MS generally or *S. mutans* in particular. Similarly, in Balakrishnan (supra), *S. salivarius* K3 is identified as active against *S. sobrinus* when grown on trypticase soy broth yeast extract calcium carbonate agar medium, but had no effect on *S. mutans*. *S. salivarius* TOVE-R (Tanzer, J. M. et al.; Infect Immun., 1985, 48:44–50) is an antagonist strain and which brought about a reduction in dental caries. There have been no reports of BLIS production by this strain.

The applicants have now identified BLIS producing *S. salivarius* strains with a broad spectrum of activity against MS dental caries causing organisms including *S. mutans*.

The present invention is broadly directed to these novel *S. salivarius* strains, and the use of anti-MS *S. salivarius* strains in the treatment of dental caries, or at least provides the public with a useful choice.

SUMMARY OF THE INVENTION

Accordingly, in one aspect, the-present invention may broadly be said to consist in a biologically pure culture of a *Streptococcus salivarius* strain which is a Salivaricin $A_2$ producer and which exhibits anti-MS activity, with the proviso that the strain is not *S. salivarius* K12 (K12).

In another aspect, the invention provides a biologically pure culture of a *Streptococcus salivarius* strain which is a Salivaricin $A_2$ producer, exhibits anti-MS activity, and for carbohydrate metabolism is positive for at least one of L-arabinose, insulin, glycogen, xylitol, and β-gentiobiose use, or β-galactosidase production; and/or is negative for at least one of glycerol, α-methyl-D-mannoside use, or alkaline phosphoaase production.

Preferably, the strain is positive for each of L-arabinose, insulin, glycogen, xylitol, and β-gentiobiose use, or β-galactosidase production; and/or is negative for each of glycerol, α-methyl-D-mannoside use, or alkaline phosphatase production.

The invention further provides a biologically pure culture of *Streptococcus salivarius* strain Mia on deposit at Deutsche Sammlung von Mikroorganismen Und Zellkulturen GmbH, Mascheroder Weg 1 b, D-38124, Braunschweig, Germany, Accession No. DSM 14685, or a culture having the identifying characteristics thereof.

The invention also provides an extract obtainable from Salivaricin $A_2$-producing strains of *S. salivarius*, which extract has anti-MS activity. In particular, the extract has anti-*S. mutans* activity. Conveniently, the extract is obtainable from *S. salivarius* strains Mia or K12.

In a further aspect, the present invention provides an antibacterial composition which includes an *S. salivarius* or extract as defined above.

In a still further aspect, the present invention provides a therapeutic formulation comprising an *S. salivarius* or extract as defined above, together with a diluent, carrier and/or excipient.

In one embodiment, the composition or formulation further comprises a secondary antibacterial agent.

In one embodiment, the therapeutic formulations are in the form of foods or drinks, preferably in the form of a dairy product-based food or drink. Alternative forms are medicaments, lozenges and confectionaries.

The invention further provides a method for at least inhibiting the growth of bacteria sensitive to *S. salivarius* of the invention, the method comprising contacting the sensitive bacteria with an inhibitory effective amount of an *S. salivarius*, extract or composition or formulation of the invention.

Preferably the sensitive bacteria are MS, and more preferably *S. mutans*.

The invention provides in another aspect a method for at least inhibiting the growth of MS or *S. mutans*, the method comprising contacting the MS or *S. mutans* with an inhibitory effective amount of:

(i) an *S. salivarius* extract composition or formulation of the invention; or (ii) *S. salivarius* K12 or an anti-MS or anti-*S. mutans* active extract therefrom, or a composition or formulation comprising K12 or an active extract therefrom.

In a further aspect, the invention provides a method of prophylactic or therapeutic treatment of dental caries caused at least in part by *S. mutans* in an individual in need thereof, the method comprising administering to said individual:

(i) an *S. salivarius*, extract, composition or formulation of the invention; or (ii) *S. salivarius* K12 or an anti-*S. mutans* active extract therefrom, or a composition or formulation comprising K12 or an active extract therefrom, in an amount effective to at least inhibit growth of *S. mutans* in the oral cavity of the individual.

In a further aspect, the invention provides a method of controlling the incidence and severity of dental caries comprising introducing into the oral cavity of an individual susceptible to dental caries, a dental caries controlling amount of an *S. salivarius*, extract, composition or formulation of the invention.

In one embodiment the dental caries is caused by MS. In that instance, *S. salivarius* K12 or an anti-MS active extract, or composition or formulation containing same may also be used.

Preferably, *S. salivarius* is administered as part of a food, drink or nutraceutical.

The methods of the invention may include the preliminary step of pre-treating the individual to at least reduce the normal microflora already present.

The invention also relates to the use of *S. salivarius* or extracts of the invention in the compositions and methods discussed above.

In another aspect, the invention also relates to the use of *S. salivarius* strains (including K12) and active extracts in the methods discussed above for inhibiting, controlling, preventing or treating dental caries caused at least in part by *S. mutans*, and more usually by MS.

Although the invention is broadly as described above, it will be appreciated by those persons skilled in the art that the invention is not limited thereto but also includes embodiments of which the following description gives examples.

DETAILED DESCRIPTION OF THE INVENTION

As noted above, the present invention is directed in a first aspect to *Streptococcus salivarius* strains which produce Salivaricin $A_2$ and which exhibit anti-MS activity. When grown on TSBCaYE agar, the *S. salivarius* strains desirably exhibit activity against a broader spectrum of MS including *S. mutans*. Salivaricin $A_2$ and an $A_2$-producing *S. salivarius* strain (strain K12) are described for example in WO 01/27143 incorporated herein by reference.

In one embodiment the invention is directed to *S. salivarius* strain Mia and *S. salivarius* strains having the identifying characteristics thereof.

Strain Mia is distinct from strain K12 in its biochemical characteristics as determined using API 20 Strep kit (bioMérieux) and API 50 CH (bioMérieux) which allow study of the carbohydrate metabolism. The differences are summarised as follows:

| API 20 Strep kit | | |
|---|---|---|
| | MIA | K12 |
| β-galactosidase | + | − |
| Alkaline phosphatase | − | + |
| API 50 CH | | |
| Glycerol | − | +anaerobic |
| L-arabinose | + | − |
| α-methyl-D-mannoside | − | +aerobic |
| Inulin | + | − |
| Glycogen | + | − |
| Xylitol | + | − |
| β-gentiobiose | + | − |

Preferably, strains for use in the invention exhibit at least one, preferably at least three, more preferably at least six, and even more preferably all of the distinguishing biochemical characteristics of strain Mia.

Mia also exhibits stronger anti-MS, and in particular stronger anti-*S. mutans* activity than K12.

*S. salivarius* strain Mia is a BLIS-producing strain with activity against other bacteria, particularly streptococci, and more particularly MS, including *S. mutans*, *S. salivarius* strain Mia was deposited with Deutche Sammlung von Mikroorganismen Und Zellkulturen GmbH, Mascheroder Weg 1 b, D-38124, Braunschweig, Germany on 12 Dec. 2001 and has been assigned Accession No. DSM 14685.

As noted above MS are considered the primary causative agents in dental caries with *S. mutans* being of particular significance. While BLIS-producing strains of *S. salvarius* active against streptococci have been reported previously, this is the first time that BLIS producing *S. salivarius* active against MS and *S. mutans* in particular, have been identified.

The *S. salivarius* strains of the invention exhibit broad spectrum antibacterial activity, particularly when grown on TSBCaYE agar media. The *S. salivarius* are therefore useful as antibacterial agents per se as well as therapeutically. In this context, "therapeutic" includes prophylactic treatment. Therapeutic uses include the treatment or prevention of microbial infections, especially streptococcal infections. The *salivarius'* of the invention are particularly suitable for use against MS and *S. mutans*. Conditions amenable to treatment with the strains or extracts of the invention include dental caries, sore throats, and bad breath.

The invention also relates to extracts obtainable from salivaricin $A_2$-producing strains of *S. salivarius* and especially from strains of the invention. These active extracts may similarly be used in therapeutic formulations and methods. Extracts can be obtained using known art protocols, conveniently by cell culture and centrifugation.

A "therapeutic formulation" is a formulation appropriate for administration of an *S. salivarius* strain or extract of the invention, to an individual in need of same, particularly a dental caries-susceptible individual. In general, therapeutic formulations of the invention are composed of an *S. salivarius* strain or extract of the invention and an acceptable carrier, diluent and/or excipient.

An "acceptable carrier, diluent and/or excipient" means a vehicle for delivery of a *S. salivarius* strain or extract of the invention, to the individual, in which the vehicle is compatible with bacterial cell viability, or activity of the extract. Acceptable carriers suitable for use in the administration of viable *S. salivarius* strains of the invention and extracts are well known to those skilled in the art. Suitable carriers are generally inert and can be either solid or liquid.

In one embodiment, the carrier is a pharmaceutically acceptable carrier. Pharmaceutically acceptable carriers suitable for use with the *S. salivarius* strains herein include, but are not limited to, water, buffered saline solutions (e.g., phosphate-buffered saline), pharmaceutically acceptable culture media (e.g. BACa, TSBCaYE agar), or other solutions which maintain the viability of the bacterium. Additionally, such pharmaceutically acceptable carriers may be aqueous or non-aqueous solutions, suspensions, and emulsions. A variety of pharmaceutically acceptable carriers suitable for oral administration of viable or lyophilized bacteria are well known in the art (see, for example, *Remington's Pharmaceutical Sciences*, 18th ed., Gennaro, ed. 1990, Mack Publishing Co., Easton, Pa., incorporated herein by reference; and the pharmaceutical composition LACTINEX™, a commercially available formulation for oral administration of viable lactobacilli). Suitable solid carriers known in the art include, for example, magnesium carbonate; magnesium stearate; celluloses; talc; sugars such as fructose, sucrose, mannitol, lactose; starches; flours; and skim milk, and similar edible powders, but are not limited thereto. Carriers for administration of extracts are similarly well known.

Typical diluents, by way of example, are: starches; lactose; mannitol; kaolin; calcium phosphate or sulphate; inorganic salts such as sodium chloride; and powdered sugars or celluloses.

The compositions may also include excipients such as tableting aids; resins; fillers; binders; lubricants; solvents; glidants; disintegrants; preservatives; buffers; flavourings; colourings; sweeteners; and fragrances as appropriate. A preferred excipient for tablet flowability and compactability is ProSolv™ (Penwest, N.Y., USA). A preferred sweetener is isomalt.

Typical binders include starch; gelatin; sugars such as lactose, fructose, and glucose; and the like. Natural and synthetic gums are also convenient, including acacia; alginates; methylcellulose; polyvinylpyrrolidine tragacanth; and the like. Polyethylene glycol; ethyl cellulose; and waxes can also serve as binders. A currently preferred binder is Emdex™ (Penwest, N.Y., USA).

Lubricants to prevent sticking to the die during formation include slippery solids such as talc, silica, magnesium and calcium stearate, polyethylene glycol, stearic acid and hydrogenated vegetable oils.

Disintegrators are substances which swell when wetted to break up the lozenge and release the *S. salivarius* or extract. The disintegrators include starches; clays; celluloses; algins and gums; more particularly corn and potato starches; methylcellulose; agar; bentonite; wood cellulose; cation exchange resins; alginic acid; guar gum; citrus pulp; carboxymethylcellulose; powdered sponge; and sodium lauryl sulfate.

The *S. salivarius* strains or extracts of the invention can be formulated in any of a variety of compositions suitable for oral administration. For example, the *S. salivarius* strains can be formulated for administration as a lyophil or cell paste prepared from a *S. salivarius* culture, or can be directly administered to the oral cavity. The strain or extract can also be administered in the form of a mouthwash, mouth rinse, toothpaste, mouthspray, gargle, capsule, lozenge, syrup, floss, chewing gum, or chewable tablet but the forms are not limited thereto.

Therapeutic formulations may include food, confectionary or drink. In one embodiment, the foodstuff or drink is a dairy product-based food or drink including by way of example, yoghurt, cheese, milk, milk power, milk biscuits, and flavoured milks. In the case of confectionary, the formulation can be a chewing gum such as described in WO 00/05972. One preferred formulation employs freeze dried *S. salivarius* of the invention in milk powder formulations in a manner similar to that previously reported for the preparation of Bifidus Milk Powder (Nagawa et al. (1988); J. Dairy Sci. 71:1777–1782).

One orally administrable formulation of *S. salivarius* is a blend of freeze dried *S. salivarius* strains with skim milk powder or the like which has been flavoured to enhance palatability.

Presently preferred orally administrable formulation of *S. salvarius*, or extracts of the invention are lozenges, chewable tablets, or capsules. Lozenges are particularly preferred. A suckable lozenge according to the invention comprises an *S. salivarius* strain or extract of the invention, isomalt and emdex. The lozenge may be prepared by direct compression, wet granulation, or dry granulation. The lozenges may be coated according to well known pharmaceutical practice.

The therapeutic formulation can additionally contain nutrients to maintain the viability of the bacterium in the formulation. As noted above, the formulation can also contain flavouring agents, colouring agents, fragrances, or other compounds which increase the palatability of the composition and/or enhance patient compliance without compromising the effectiveness of the formulation. Methods for preparation of formulations for oral administration are well known in the art (see, for example, Remington's Pharmaceutical Sciences, 18th ed., supra, incorporated herein by reference).

For general antimicrobial use, formulations may also be produced for other methods of administration including topically administrable formulations but not limited thereto.

K12 and active extracts thereof discussed above may similarly be prepared as above, including in the compositions and formulations discussed.

The formulations and compositions of the invention may further comprise one or more secondary antibacterial agents. These secondary agents may, for example, be antibiotics, or other antibacterial agent or antibacterial producing microorganisms. Useful antibacterials include nisin, and other BLIS for example. Preferably, the secondary antibacterial agent is a BLIS or BLIS producing microorganism. The BLIS may be one or more of *salivaricin* A, $A_1$, $A_2$ and B. Other antibacterial microorganisms include known *S. salivarius* such as K12 and K30.

*S. salivarius* strains of the invention are primarily found on the tongue surface. Combinations with *S. salivarius* that grow in dental plaque such as TOVE-R (supra) would be useful.

The formulation and compositions of the invention may additionally comprise other anti-carcinogenic agents, for example, xylitol, fluoride, Manuka honey, and tannins.

In the treatment of dental caries, *S. salivarius* strains or extracts of the invention can be administered to any dental caries-susceptible individual, usually an individual in which *S. mutans* or MS colonises the oral cavity such that the dental caries is caused at least in part by *S. mutans* and more commonly by MS.

The term "individual" as used herein includes humans, horses, dogs, cats, pigs, sheep, cattle, goats but is not limited thereto. Preferably, the individual is a human. The *S. salivarius* strains can be administered to the individual at any age, e.g. childhood, adolescence, or adulthood.

The *S. salivarius* of the invention or K12 can be orally administered in a variety of ways. For example, in the form of compositions or formulations discussed above, or as suspensions, sustained release formulas (e.g. an oral implant containing the *S. salivarius* strain) or lyophil powders. The *S. salivarius* strains can also be administered by direct application of a lyophil, culture, or cell paste to the teeth or tongue of the individual. Any mode of administration is suitable as long as the therapeutic formulation is applied to the oral cavity. In one embodiment, the *S. salivarius* or extracts are administered by applying directly to the teeth of the individual, e.g. by brushing and/or flossing.

In general, the amount of *S. salivarius* administered to the individual will be an amount effective for replacement of dental caries-causing MS strains, or at least *S. mutans* in the oral cavity of the host. "An amount effective for replacement of dental caries-causing MS strains or at least *S. mutans* in the oral cavity of the host" means an amount effective for oral cavity colonisation by the *S. salivarius* strain, and significant reduction of the resident dental caries-causing *S. mutans* or MS strains (e.g. by competition between the bacteria for nutrients and/or by the production of BLIS by the *S. salivarius* strain).

The term "unit dose" when used in reference to a therapeutic formulation of the present invention refers to physically discrete units suitable as unitary dosage for the individual, each unit containing a predetermined quantity of active material (viable *S. salivarius* or active extract thereof)

calculated to produce the desired therapeutic effect in association with the required diluent, carrier, or excipient.

Specific dosages can vary widely according to various individual variables including size, weight, age, disease severity (e.g. the tenacity and/or number of dental caries-causing resident MS) and responsiveness to therapy (e.g. the susceptibility of the individual's oral cavity to colonisation). Methods for determining the appropriate route of administration and dosage may be determined by the consumer as they deem appropriate, or on a case-by-case basis by an attending dentist or other clinician. Such determinations are routine to one of ordinary skill in the art (see for example, *Remington's Pharmaceutical Sciences,* 8th ed., Gennaro, ed., Mack Publishing Company, Easton, Pa., 1990).

In general, the number of *S. salivarius* administered to the individual will range from about $10^2$ to $10^{15}$ bacteria, preferably from about $10^3$ to $10^{14}$ bacteria, more preferably from about $10^5$ to $10^{12}$ bacteria, normally about $10^9$ to $10^{10}$ colony forming units (CFU) per dose. One lozenge formulation employs $3.8 \times 10^9$ CFU/ml.

Multiple doses of the *S. salivarius* strain can be administered to achieve oral cavity colonisation and replacement of the resident, dental caries-causing MS strains, particularly *S. mutans*, of the individual. The *S. salivarius* strain or extract may need to be administered to the patient once only or repeatedly. Repeat treatments may be once a month, once a week, once a day, twice a day, or as may otherwise be required. Conveniently, the administration may be effected as part of the patient's routine dental care, e.g. as a component of a lozenge, gum, toothpaste, floss, or mouthwash.

To facilitate colonisation, in one embodiment the treatment method of the invention includes a preliminary step of pre-treating the individual to at least reduce the normal microflora present in the oral cavity, including dental caries causing organisms. This pre-treatment comprises the step of administering an antimicrobial agent such as chlorhexidine, lactoperoxidase, green tea, or pineapple juice (freeze dried), but not limited thereto, or may follow a prescribed course of antibiotics such as penicillin, erythromycin, or amoxycillin administered to said individual. *S. salivarius* of the invention or *S. salivarius* K12 is then administered to the depopulated environment to repopulate same.

A currently preferred treatment protocol for dental caries comprises pre-treatment by brushing teeth with chlorhexidine gel for 2 to 5 days, preferably 3 days. A lozenge is administered 1–4 hours, preferably 2 hours after the gel. This is followed by administration of a further 2–5, preferably 3 lozenges through the day at intervals of 1–4 hours, preferably every 2 hours. This protocol is followed for 2–4 days to facilitate colonisation. For maintenance purposes 1, 2, or 3 lozenges, usually 1 to 2 lozenges are taken each day following ordinary tooth brushing. The regime is continued for as long as required.

Successful colonisation of the individual's oral cavity by the *S. salivarius* strain can be established by culturing the bacteria of the individual's oral cavity, and identifying the *S. salivarius* strain by, for example, BLIS production or other methods well known in the art for bacterial strain identification.

The methods and uses of the invention may further comprise the use of one or more secondary antibacterial agents, and/or anticariogenic agents as discussed above.

Where the term comprise, comprises, comprised or comprising are used in this specification, they are to be interpreted as specifying the presence of the stated features, integers, steps or components referred to, but not to preclude the presence or addition of one or more other features, integers, steps, components or groups thereof.

Various aspects of the invention will now be illustrated in a non-limiting way by reference to the following experimental section.

EXPERIMENTAL

Identification

Strain Mia was isolated from the oral cavity of a healthy adult human subject. It grows on Mitis salivarius agar at 37° C., 5% $CO_2$ with morphology typical of *S. salivarius* as follows:
Colony shape and size: round, 1–2 mm in diameter
Margin (edge): entire (smooth)
Elevation: convex
Colour: blue
Texture: mucoid On Blood agar [Columbia Agar Base (GIBCO) with 5% human blood] at 37° C., 5% $CO_2$ it is not haemolytic, and exhibits the following morphology:
Colony shape and size: round, <1 mm in diameter
Margin (edge): entire (smooth)
Elevation: convex
Colour: white
Texture: mucoid When cultivated on either Blood agar or on Trypticase soy broth (BBL)+Davis agar 1.5% supplemented with 0.1% calcium carbonate the bacterial growth appears relatively more firmly adherent to the agar surface than is typical of most *S. salivarius*. The API 20 Strep Identification code for the strain is 5050451, which corresponds to *Streptococcus salivarius* (98.4% identity).

16s rRNA Sequence Analysis with reference to the GENEBANK database established the strain to be *Streptococcus salivarius* (99.9% homology).

Biochemical Characterization

Biochemical characterization of *S. salivarius* MIA was conducted using the API 20 Strep kit (bioMérieux) and API 50 CH (bioMérieux) which allows the study of the carbohydrate metabolism.

The API 20 Strep results are as follows:

| | |
|---|---|
| Acetone production | positive |
| Hydrolysis | negative |
| β-glucosidase | positive |
| Pyrrolidonyl arylamidase | negative |
| α-galactosidase | negative |
| β-gluuronidase | negative |
| β-galactosidase | positive |
| alkaline phosphatase | negative |
| Leucine arylamidase | positive |
| Arginine dihyrolase | negative |
| Ribose | negative |
| L-arabinose | negative |
| Mannitol | negative |
| Sorbitol | negative |
| Lactose | positive |
| Trehalose | positive |
| Inulin | negative |
| Raffinose | positive |
| Starch | weak positive |
| Glycogen | negative |
| β-haemolytic | negative |

The API 50 CH results are as follows:

| | |
|---|---|
| Glycerol | negative |
| Erythritol | negative |
| D-Arabinose | negative |
| L-Arabinose | positive (anaerobic only) |
| Ribose | negative |

-continued

| | |
|---|---|
| D-Xylose | negative |
| Adonitol | negative |
| β Methyl-xyloside | negative |
| Galactose | positive |
| D-Glucose | positive |
| D-Fructose | positive |
| D-Mannose | positive |
| L-Sorbose | negative |
| Rhamnose | negative |
| Dulcitol | negative |
| Inositol | negative |
| Mannitol | negative |
| Sorbitol | negative |
| α Methyl-D-mannoside | negative |
| α Methyl-D-glucoside | positive (anaerobic only) |
| N-Acetyl glucosamine | positive |
| Amygdaline | positive |
| Arbutin | positive |
| Esculin | positive |
| Salicin | positive |
| Cellobiose | positive |
| Maltose | positive |
| Lactose | positive |
| Melibiose | positive (aerobic only) |
| Saccharose | positive |
| Trehalose | positive |
| Inulin | positive (anaerobic only) |
| Melezitose | negative |
| D-Raffinose | positive |
| Amidon | positive |
| Glycogen | positive (anaerobic only) |
| Xylitol | positive (aerobic only) |
| β Gentiobiose | positive |
| D-Turanose | negative |
| D-Lyxose | negative |
| D-Tagatose | positive (anaerobic only) |
| D-Fucose | negative |
| L-Fucose | negative |
| D-Arabitol | negative |
| L-Arabitol | negative |
| Gluconate | negative |
| 2 ceto-gluconate | negative |
| 5 ceto-gluconate | negative |

*S. salivarius* MIA is urease positive when grown on Christenens urea agar.

Inhibitory Activity

Deferred Antagonism Test for BLIS Activity

When tested for bacteriocin-like inhibitory substance (BLIS) production on the Blood agar-based medium, Columbia agar Base (GIBCO)+0.1% $CaCO_3$+5% human blood (BACa) according to the deferred antagonism test of Tagg and Bannister the P-type designation of strain Mia is 677.

P-type of *S. salivarius* MIA

Producer typing (P-type) describes the antimicrobial activity of bacteria against a set of standard indicators. The procedure was first described by Tagg and Bannister (J. Med. Microbiol. 1979; 12: 397–411).

For P-typing *S. salivarius* MIA was grown as a diametric streak culture on a Blood agar+0.1% calcium carbonate plate or Trypticase soy-yeast extract-calcium carbonate agar (Trypticase soy broth, 30; yeast extract, 20 g; calcium carbonate, 2.5 g; agar, 15 g; distilled water, 1000 ml), incubated at 37° C., 5% $CO_2$ for 18 h. The growth was then removed and the surface of the plate sterilised with chloroform. Nine indicator strains were then cross-inoculated. After incubation at 37° C., 5% $CO_2$ for 18 h inhibition of growth was recorded. The inhibition patterns were recorded in a code form by considering the nine indicators as three triplets (eg, I1, I2, I3, I4, I5, I6; I7, I8, I9). Positive reactions against each were given a score of 4, 2 or 1 depending on whether the indicator was, respectively, the first, second or third member of the triplet. No inhibition was recorded as zero. The total score of each triplet thus specified uniquely the reactions against the three indicators. The complete P-type code is written as a sequence of three numbers, consecutively defining the reactions within the three triplets.

*S. salivarius* MIA has a 677 P-type on Blood agar+ calcium carbonate, and a 777 P-type on Trypticase soy-yeast extract-calcium carbonate agar.

This corresponds to inhibition of all 9 bacteria in the panel of 9 indicator strains except for indicator 3. This pattern is typical of that given by *salivaricin* A- producing *S. salivarius* such as strain 20P3 (Ross et al Appl. Envir. Microbiol. 1993; 59;2014). However, when tested on trypticase soy broth (BBL)+Davis Agar (1.5%)+0.25% calcium carbonate+yeast extract (2%) [TSBCaYE] the P-type is 777 (i.e. all 9 indicators are inhibited). Associated with this increased activity against indicator 3 there is also additional activity against a variety of other bacteria when tested as indicators (Table 1).

TABLE 1

Antimicrobial activity of strain Mia on BACa and TSCaYE media

| Bacteria | | Susceptibility when tested on | |
|---|---|---|---|
| | | BACa | TSBCaYE |
| *Clostridium sporogenes* | | + | + |
| *Clostridium perfringens* | | + | + |
| *Actinomyces viscosus* | T14 | + | + |
| | M100 | + | + |
| *Actinomyces naeslundii* | 10301 | + | + |
| *Streptococcus sobrinus* | OMZ176 | − | + |
| *Streptococcus mutans* | ATCC10449 | − | + |
| | OMZ175 | − | + |
| | 633K | − | + |
| | H7 | − | + |
| | 13M | − | + |
| | E49 | − | + |
| | K58 | − | + |
| | K60 | − | + |
| | M46 | − | + |
| | MUTI | − | + |
| | MUTII | − | + |
| *Corynebacterium diphtheriae* | gravis | − | + |
| *Enterococcus faecalis* | 98 | − | + |
| *Enterococcus hirae* | 9790 | − | + |
| *Streptococcus agalactiae* | 211B | + | + |
| | P3 | + | + |
| *Streptococcus uberis* | I4 | + | + |
| | D618 | + | + |
| *Lactobacillus brevis* | | − | + |
| *Lactobacillus casei* | | − | + |
| *Lactobacillus acidophilus* | | + | + |
| *Streptococcus pneumoniae* | PK2 | + | + |
| | PK34 | + | + |
| *Moraxella catarrhalis* | 4 | − | + |
| | K | − | + |
| *Listeria monocytogenes* | 10403 | + | + |
| *Listeria monocytogenes* | 215 | + | + |
| *Stomatococcus mucilagenosus* | Coup | + | + |
| *Neisseria gonnorhoea* | | − | + |
| *Neisseria meningitidis* | | − | + |
| *Neisseria lactamica* | | − | + |
| *Haemophilus influenzae* | 30 | − | + |
| | 37 | − | + |
| *Staphylococcus saprophyticus* | 7292 | − | + |
| *Staphylococcus cohnii* | 20260 | − | + |

Deferred Antagonism Test of Anti-*S. mutans* Activity

The anti-*S. mutans* spectrum of inhibitory activity of *salivaricin* $A_2$ producer strains was established by use of a deferred antagonism test, essentially as described by Tagg and Bannister [J. Med. Microbiol. 1979;12:397]. In brief, a 1-cm wide diametric streak culture of each producer strain was inoculated onto TSBCa and BACa media either with or without yeast extract (YE) supplementation. Following incubation in an anaerobic atmosphere for 24 hours at 37° C. the macroscopic cell growth was removed with a glass slide and residual cells on the agar surface were killed by exposure to chloroform vapours for 30 minutes. The agar surface was then aired for 30 minutes and the indicator strained inoculated from 18 hour Todd Hewitt Broth (THB) cultures across the line of the original streak culture with use of cotton swabs. After incubation for 18 hours in 5% (v/v) $CO_2$ at 37° C. the extent of inhibition of each indicator stain was recorded.

| TSBCaYE medium (per 500 ml) | |
| --- | --- |
| Trypticase soy broth (BBL) | 15 g |
| Davis Agar | 7.5 g |
| Yeast Extract (Difco) | 10 g |
| $CaCO_3$ | 1.25 g |
| BACaYE medium (per 500 ml) | |
| Columbia Blood Agar base (Difco) | 22 g |
| $CaCO_3$ | 0.5 g |
| Yeast Extract (Difco) | 10 |

The results are shown in Table 2.

TABLE 2

Comparison of anti-*S. mutans* activity of *S. salivarius* strains Mia and K-12 in deferred antagonism tests on BACa or TSBCa when supplemented with yeast extract

| Producer strain | Salivaricin status | Test medium | Inhibition of *S. mutans* strain | | | | | | | | |
| --- | --- | --- | --- | --- | --- | --- | --- | --- | --- | --- | --- |
| | | | ATCC 10449 | OMZ 175 | H7 | 13M | K-56 | K-60 | M-46 | MutI | MutII |
| Mia | A2 | BaCa | +++ | +++ | ++ | − | − | − | ++ | − | − |
| Mia | | BaCaYE | +++ | +++ | ++ | ++ | ++ | ++ | ++ | ++ | ++ |
| Mia | | TSBCa | ++ | +++ | + | − | − | − | + | + | − |
| Mia | | TSBCaYE | +++ | +++ | ++ | + | + | + | ++ | + | + |
| K-12 | A2 + B | BaCa | ++ | ++ | − | − | − | + | + | − | − |
| K-12 | | BaCaYE | +++ | +++ | +++ | ++ | ++ | ++ | +++ | ++ | ++ |
| K-12 | | TSBCa | ++ | ++ | − | − | − | − | ++ | − | − |
| K-12 | | TSBCaYE | ++ | ++ | ++ | − | + | + | ++ | + | − |

Production of Inhibitory Activity in Saliva Fluid by Strain Mia

Saliva fluid was prepared as follows:

Stimulated saliva was collected, heated at 60° C. for 0.5 hr then centrifuged at 12000×g for 10 min. The supernatant was supplemented with 0.5% maltose, 0.5% $CaCO_3$ and 0.25 µg/ml cysteine (final concentrations).

The supplemented supernatant was used as a basal fluid medium for growth of strain Mia at 37° C. The inoculum was from an 18 h TSBYECa culture at a ratio of 100 µl per 2 ml supernatant. Different aliquots were supplemented as indicated.

After 24 h incubation in an anaerobic atmosphere samples of the saliva cultures were tested for inhibitory activity against the indicators OMZ175, MutII, and I1 either neat or following 10× concentration by rotary evaporation. The 10× concentrated supernatant from the culture grown in saliva supplemented with Maltose, Cysteine and $CaCO_3$ had inhibitory activity against *S. mutans* strain OMZ175 as shown in the table below. *S. salivarius* Mia therefore produces anti-*S. mutans* activity when grown in saliva.

Assay of Inhibitory Activity

Inhibitory activity was determined by end-point titration using a surface spot method in which 20 µL drops of two-fold serial dilutions of the test preparation in saline were spotted onto the surface of Blood Agar medium. When the drops had dried into the agar, the surface of the medium was sterilized by exposure to chloroform vapour for 30 minutes, aired and then inoculated by swabbing evenly from an 18 hour THB culture of indicator strain. Following incubation, the titre of inhibitory activity in Arbitrary Units (AU) per mL was taken to be the reciprocal of the highest dilution to show definite inhibitory activity. The results are shown in Table 3.

TABLE 3

Production of inhibitory activity in saliva fluid by strain Mia

| | Activity (AU/ml) against indicator of supernatant of saliva fluid culture: | | | | | |
| --- | --- | --- | --- | --- | --- | --- |
| | Unconcentrated | | | Concentrated × 10 speedvac | | |
| Supplement | I1 | OMZ175 | Mut II | I1 | OMZ175 | Mut II |
| Saliva only | 0 | 0 | 0 | 1 | 0 | 0 |
| M | 0 | 0 | 0 | 1 | 0 | 0 |
| M, Cy | 0 | 0 | 0 | 1 | 0 | 0 |
| M, Ca | 2 | 0 | 0 | 2 | 0 | 0 |
| Cy, Ca | 0 | 0 | 0 | 0 | 0 | 0 |
| M, Cy, Ca | 4 | 0 | 0 | 4 | 2 | 0 |

M = 0.5% maltose;
Cy = 0.5% cysteine;
Ca = 0.1% $CaCO_3$

In vivo Activity of *S. salivarius* MIA Against. MS.

One subject brushed their teeth with 2% chlorhexidine gel for 2 minutes on the first day and then sucked a tablet containing $3.8 \times 10^9$ colony forming units of *S. salivarius* MIA, two hours after the chlorhexidine treatment and then a further three tablets at two hourly intervals. On the second day the subject repeated the same procedure as for day one. The subject for the remaining 25 days of the trial sucked one tablet after brushing their teeth with a commercial toothpaste, in the morning and at night.

Control subjects cleaned their teeth once a day for three days with 2% chlorhexidine gel and for the remaining time brushed their teeth with a commercial toothpaste.

Saliva samples were collected from all subjects prior to starting the trial and at intervals throughout the trial to determine number of MS (colony forming units (cfu) per ml of saliva). The saliva sample was diluted in sterile saline and spiral plated onto Mutans selective agar, and the plates incubated under anaerobic conditions at 37° C. for 2 days. The number of *S. salivarius* MIA in the saliva sample was also determined for the subject taking the tablets. The diluted saliva sample is spiral plated onto Mitis-*salivarius* agar and the plates are incubated at 37° C., 5% $CO_2$ for 18–24 hours. The number of *S. salivarius* colonies are then counted. To determine the percentage of colonization with *S. salivarius* MIA the following protocol is used. Fresh THB cultures of *Micrococcus luteus* and *S. mutans* OMZ175 are spread separately on the top of a Blood agar/calcium plates. *S. salivarius* colonies are then picked into both plates. The plates are incubated at 37° C., 5% $CO_2$ for 18–24 hours. *S. salivarius* MIA colonies produce zones of inhibition around the stab cultures on both plates. Percentage colonization is determined as the number of positive colonies divided by the total number of colonies picked.

Brushing teeth with a 2% chlorhexidine gel resulted in a 1.7–2.4 log reduction in MS counts in both the control (Table 4) and the colonizing subject (Table 5). The MS cell counts in the control subjects increased to pre-treatment levels, in the control subjects, between one to six days after brushing with the gel. The test subject was 100% colonized after the pre-treatment with the gel and remained highly colonized for the remaining trial period (Table 5). Numbers of MS were still 1.7 log lower than pre-treatment levels at 27 days. This shows that colonization with *S. salivarius* MIA is capable of preventing the re-establishment of high levels of MS.

TABLE 4

The effect of 2% chlorhexidine gel on the levels of MS in the control subjects

| Time | Number of MS (cfu/ml of saliva) | | | |
|---|---|---|---|---|
| (days) | Subject 1 | Subject 2 | Subject 3 | Subject 4 |
| Pre-treatment | $1.4 \times 10^4$ | $1.3 \times 10^5$ | $5.8 \times 10^3$ | $9.9 \times 10^3$ |
| 1 | $2.2 \times 10^3$ | $1.2 \times 10^3$ | $1.5 \times 10^2$ | $4.3 \times 10^1$ |
| 2 | $3.0 \times 10^2$ | ns | $<10^2$ | $4.0 \times 10^3$ |
| 5 | $4.5 \times 10^2$ | $3.3 \times 10^4$ | $2.3 \times 10^3$ | $3.7 \times 10^4$ |
| 8 | $8.4 \times 10^4$ | ns | $5.1 \times 10^4$ | ns |
| 33 | $2.7 \times 10^3$ | ns | $3.5 \times 10^4$ | $2.0 \times 10^3$ |

TABLE 5

Effect of colonization with *S. salivarius* MIA on MS

| Time (days) | % colonization with *S. salivarius* MIA | Number of MS (cfu/ml of saliva) |
|---|---|---|
| Pre-treatment | 0 | $5.8 \times 10^4$ |
| 1 | | $2.5 \times 10^2$ |
| 2 | | $1.0 \times 10^2$ |
| 3 | | $4.0 \times 10^2$ |
| 6 | 100 | $2.0 \times 10^2$ |
| 13 | 98 | $2.0 \times 10^2$ |
| 16 | 100 | $6.0 \times 10^2$ |
| 20 | 100 | $8.0 \times 10^2$ |
| 23 | 95 | $2.6 \times 10^3$ |
| 27 | 100 | $1.0 \times 10^3$ |

Preparation of Anti-MS Active Extract

One hundred ml of molten Trypticase Soy agar containing 2% yeast extract and 0.25% calcium carbonate was poured into a 1 L schott bottle. One ml of an overnight culture of *S. salivarius* MIA, grown in Todd Hewitt broth at 37° C., in 5% $CO_2$ in air, was added to the bottle. The culture was incubated anaerobically at 37° C. for 18–24 hours. One hundred ml of Trypticase Soy broth containing 2% yeast extract and 0.25% calcium carbonate was added to the bottle, which had been preincubated under anaerobic conditions. The culture was then incubated for a further 24 hours anaerobically at 37° C. The broth was centrifuged to remove the bacterial cells and then ammonium sulphate was added to 50% (w/v) and incubated at 4° C. for 18 hours. The sample was then centrifuged and the pellet resuspended in 1 ml of milli-Q water. Anti-MS activity of the sample was then tested using a well diffusion assay in Blood agar plates. Fifty µl of the sample is added to each well and air-dried. The plates were then chloroform treated. An overnight culture of the indicator strain was spread over the top of the plate and incubated at 37° C., 5% $CO_2$ in air, for 18–24 hours.

Zones of inhibition (distance from edge of the well to edge of inhibition of cell growth) were recorded against all the indicator strains (Table 6).

TABLE 6

Well diffusion assay of *S. salivarius* MIA extract

| Indicator strain | Zone of inhibition (mm) |
|---|---|
| *Micrococcus luteus* T18 | 12 |
| *Streptococcus anginosus* T29 | 2 |
| *Streptococcus mutans* H7 | 2 |
| *Streptococcus mutans* 10449 | 3 |
| *Streptococcus mutans* MutII | 2 |
| *Streptococcus mutans* OMZ175 | 2 |

DOSAGE FORM EXAMPLE

Lozenge

| Ingredients | Per 945 mg lozenge |
|---|---|
| *S. salivarius* | $3.8 \times 10^9$ CFU (freeze dried) |
| Isomalt | 600 mg |
| Emdex ™ | 150 mg |
| ProSolv HD ™ | 50 mg |
| Magnesium stearate | 15 mg |
| Flavour | 10 mg |

The ingredients are blended and tablets produced using dry compression.

INDUSTRIAL APPLICATION

The results above demonstrate the antibacterial effect of *S. salivarius* strains, particularly strain Mia against a broad spectrum of microorganisms, particularly *streptococci*. These strains are the first BLIS producing *S. salivarius* to be identified which have activity against MS, and more particularly *S. mutans*. The strains and related active extracts herein therefore have application in methods of therapeutically treating individuals against the harmful effects of *streptococcus* infection, especially in the oral cavity. These methods include treatment of dental caries in which MS or *S. mutans* are the primary causative agent. The *S. salivarius* extracts and compositions of the invention also have application in the treatment of bad breath and sore throats.

It will be appreciated that the above description is provided by way of example only and that variations in both the materials and techniques used which are known to those persons skilled in the art are contemplated.

The invention claimed is:

1. A biologically pure culture of *Streptococcus salivarius* strain Mia on deposit at Deutsche Samrnlung von Mikroorganismen Und Zeilkulturen GmbH, Mascheroder Weg 1 b, D-38124, Braunschweig, Germany, Accession No. DSM 14685.

2. An antibacterial composition comprising a biologically pure culture of *Streptococcus salivarius* strain Mia on deposit at Deutsche Sanimlung von Mikroorganismen Und Zellkulturen GmbH, Mascheroder Weg 1 b, D-38124, Braunschweig, Germany, Accession No. DSM 14685.

3. The composition as claimed in claim 2, together with a diluent, carrier and/or excipient.

4. The composition as claimed in claim 2, which is a therapeutic formulation.

5. The composition as claimed in claim 2, which further comprises one or more secondary antibacterial agents.

6. The composition as claimed in claim 2, which further comprises one or more secondary antibacterial agents selected from nisin, BLIS and BLIS producing microorganisms.

7. The composition as claimed in claim 6, wherein the BLIS producing microorganism is K12 and/or K30.

8. The composition as claimed in claim 2, which further comprises one or more BLIS selected from salivaricin A, $A_1$, $A_2$ and B.

9. The composition as claimed in claim 2, which further comprises one or more secondary anti-cariogenic agents.

10. The composition as claimed in claim 2, which further comprises one or more secondary anti-cariogenic agents selected from xylitol, fluoride, Manuka honey and tannin.

11. The composition as claimed in claim 2, which is an orally administrable composition.

12. The composition as claimed in claim 2, wherein the composition is included in a food or drink.

13. The composition as claimed in claim 2, wherein the composition is included in a dairy based food or drink.

14. The composition as claimed in claim 2, wherein the composition is included in milk powder, milk biscuits, milk, flavoured milk, yoghurt or cheese.

15. The composition as claimed in claim 2, wherein the composition is in the form of medicaments, lozenges or confectionaries.

16. The composition as claimed in claim 2, which is in the form of a lozenge.

17. The composition as claimed in claim 2, which is in a mouthwash, mouth rinse, toothpaste, gargle, syrup, mouth spray, capsule, floss, chewing gum, or tablet.

18. The composition as claimed in claim 2, which is in unit dosage form.

19. The composition as claimed in claim 18, which contains from about $10^5$ to about $10^{12}$ CFU of *S. salivarius* strain Mia per dose.

20. The composition as claimed in claim 19, which contains from about $10^9$ to about $10^{10}$ CFU of *S. salivarius* strain Mia per dose.

21. A method for inhibiting in the oral cavity of an individual the growth of bacteria sensitive to *Streptococcus salivarius* strain Mia on deposit at Deutsche Sammlung von Mikroorganismen Und Zellkulturen GmbH, Mascheroder-Weg 1b, D-38124, Braunschweig, Germany, Accession No. DSM 14685, the method comprising pre-treating the individual with an effective amount of an antimicrobial or antibiotic to reduce the microflora already present and administering to the oral cavity of the individual an inhibitory effective amount of said *S. salivarius* strain Mia.

22. The method as claimed in claim 21 wherein the sensitive bacteria are MS.

23. The method as claimed claim 21 wherein the sensitive bacteria are *S. mutans*.

24. The method as claimed in claim 21, wherein the antimicrobial is chlorhexidene.

25. A method of controlling the incidence or severity of dental caries comprising the steps of:
    (a) administering to a patient an amount of an antibiotic or antimicrobial effective to reduce microflora including dental caries causing organisms present, thereby resulting in a bacterially depopulated environment; and
    (b) administering to the oral cavity of the patient, the *S. salivarius* strain Mia as claimed in claim 1, or a composition or formulation comprising said *S. salivarius* strain Mia; to repopulate said environment.

* * * * *